US012810973B2

(12) United States Patent
Darshana Govind et al.

(10) Patent No.: US 12,810,973 B2
(45) Date of Patent: Nov. 24, 2026

(54) RADIOMIC ARTIFICIAL INTELLIGENCE FOR NEW TREATMENT RESPONSE PREDICTION

(71) Applicant: Janssen Research & Development, LLC, Raritan, NJ (US)

(72) Inventors: Fnu Darshana Govind, San Jose, CA (US); Stephen Yip, Boston, MA (US)

(73) Assignee: Janssen Research & Development, LLC, Raritan, NJ (US)

(*) Notice: Subject to any disclaimer, the term of this patent is extended or adjusted under 35 U.S.C. 154(b) by 230 days.

(21) Appl. No.: 18/234,237

(22) Filed: Aug. 15, 2023

(65) Prior Publication Data

US 2024/0055081 A1 Feb. 15, 2024

Related U.S. Application Data

(60) Provisional application No. 63/398,204, filed on Aug. 15, 2022.

(51) Int. Cl.
*G16H 10/20* (2018.01)
*G06T 7/00* (2017.01)
*G16H 20/00* (2018.01)

(52) U.S. Cl.
CPC ........... *G16H 10/20* (2018.01); *G06T 7/0012* (2013.01); *G16H 20/00* (2018.01); *G06T 2207/10081* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

| | | | | |
|---|---|---|---|---|
| 6,364,907 | B1 * | 4/2002 | Obochi | A61K 41/0057 435/325 |
| 2021/0042916 | A1 * | 2/2021 | Zhang | A61B 6/50 |
| 2021/0090694 | A1 * | 3/2021 | Colley | G16H 10/40 |
| 2021/0097439 | A1 * | 4/2021 | Vodencarevic | G06F 8/71 |

(Continued)

FOREIGN PATENT DOCUMENTS

| | | |
|---|---|---|
| WO | 2020/185660 | 9/2020 |
| WO | 2021/053135 | 3/2021 |

OTHER PUBLICATIONS

He, K. et al., "Deep Residual Learning for Image Recognition," arXiv:1512.03385v1, Dec. 10, 2015, 12 pages.

(Continued)

*Primary Examiner* — Tsung Yin Tsai
(74) *Attorney, Agent, or Firm* — MASCHOFF BRENNAN; Elaine K. Lee

(57) ABSTRACT

A deep learning pipeline can be configured to use medical image data to generate predictions of therapeutic responses to a new treatment in members of a cohort of interest of treatment candidates. A plurality of respective deep learning networks may be trained using respective medical image datasets having respective degrees of relevance to the cohort of interest. Learned parameters of one deep learning network may be transferred in succession to another deep learning network after training the one deep learning network with a one of the respective medical image datasets and before training the other deep learning network with another medical image dataset of the respective medical image datasets.

18 Claims, 7 Drawing Sheets

(56) References Cited

U.S. PATENT DOCUMENTS

| | | | | |
|---|---|---|---|---|
| 2021/0326653 | A1* | 10/2021 | Zhou | G06F 18/2155 |
| 2022/0022800 | A1* | 1/2022 | Abrams | A61B 5/372 |
| 2022/0230300 | A1* | 7/2022 | Kawczynski | G06T 7/0004 |
| 2023/0377747 | A1* | 11/2023 | Molero Leon | G16H 40/67 |
| 2025/0139767 | A1 | 5/2025 | Ramon et al. | |

OTHER PUBLICATIONS

Chen, T. et al., "A Simple Framework for Contrastive Learning of Visual Representations," Proceedings of the 37th International Conference on Machine Learning, Vienna, Austria, PMLR 119, 2020, 11 pages.

Ilse, M. et al., "Attention-based Deep Multiple Instance Learning," arXiv:1802.04712v4 [cs.LG], Jun. 28, 2018, 16 pages.

Anthimopoulos, M. et al., "Lung Pattern Classification for Interstitial Lung Diseases Using a Deep Convolutional Neural Network," IEEE Transactions on Medical Imaging, vol. 35, No. 5, May 2016, pp. 1207-1216, 10 pages.

Hosny, A. et al., Deep learning for lung cancer prognostication: A retrospective multi-cohort radiomics study. PLOS Medicine, Nov. 30, 2018, 25 pages.

Cheplygina, V. et al., "Not-so-supervised: a survey of semi-supervised, multi-instance, and transfer learning in medical image analysis", arXiv:1804.06353v2 [cs.CV] , Apr. 17, 2018, 19 pages.

Napel, S. et al., "Quantitative Imaging of Cancer in the Postgenomic Era: Radio(geno)mics, Deep Learning, and Habitats," Cancer, vol. 124, No. 24, Dec. 2018, Epub Nov. 1, 2018, pp. 4633-4649.

Cha, S. et al., "Attention-Based Transfer Learning for Efficient Pneumonia Detection in Chest X-ray Images," Applied Sciences, vol. 11, No. 3, Jan. 29, 2021, 1242, 15 pages.

Feng, B. et al. , "A Transfer Learning Radiomics Nomogram for Preoperative Prediction of Borrmann Type IV Gastric Cancer From Primary Gastric Lymphoma," Frontiers in Oncology, vol. 11, Jan. 11, 2022, 11 pages.

International Search Report and Written Opinion, dated Oct. 13, 2023, for International Application No. PCT/IB2023/058199, 11 pages.

Lu, M. et al., "Semi-Supervised Histology Classification using Deep Multiple Instance Learning and Contrastive Predictive Coding," arXiv: 1910.10825, 2019, 8 pages.

Loeffler, L. et al., "Artificial Intelligence-Based Detection of FGFR3 Mutational Status Directly from Routine Histology in Bladder Cancer: A Possible Preselection for Molecular Testing?" European Urology Focus, vol. 8(2), 2021, pp. 472-479.

"FGFR Mutation and Fusion Analysis, Tumor," Mayo Clinic Laboratories, 2020, 2 pages.

Coudray, N. et al. "Classification and mutation prediction from non-small cell lung cancer histopathology images using deep learning," Nature Medicine, 2018, vol. 24 (10), 23 pages.

Yun, J. et al. "Antitumor Activity of Amivantamab (JNJ-61186372), an EGFR-MET Bispecific Antibody, in Diverse Models of EGFR Exon 20 Insertion-Driven NSCLC," Cancer Discovery, vol. 10 (8), 2020, pp. 1195-1209.

Liang, H. et al. "MET Oncogene in Non-Small Cell Lung Cancer: Mechanism of MET Dysregulation and Agents Targeting the HGF/c-Met Axis", Oncotargets and Therapy, vol. 13, 2020, pp. 2491-2510.

Yoni, S. et al. DeepSMILE: Self-supervised heterogeneity-aware multiple instance learning for DNA damage response defect classification directly from H&E whole slide images:, Arxiv.org, Cornell University Library, 2021, 16 pages.

Dehaene, O. et al. "Self-Supervision Closes the Gap Between Weak and Strong Supervision in Histology", Arxiv.org, Cornell University Library, 2020, 15 pages.

International Search Report and Written Opinion, dated Dec. 9, 2022, for International Application No. PCT/IB2022/058892, 5 pages.

Communication pursuant to Article 94(3) EPC, dated Jul. 29, 2025, for EP Application No. 22777359.5, 10 pages.

* cited by examiner

6000

RADIOMIC ARTIFICIAL INTELLIGENCE FOR NEW TREATMENT RESPONSE PREDICTION

CROSS-REFERENCE TO RELATED APPLICATIONS

This application claims the benefit of U.S. Provisional Application No. 63/398,204 filed on Aug. 15, 2022. The contents of that application are incorporated by reference herein.

BACKGROUND

This disclosure relates generally to technology for computerized prediction of treatment response using medical images.

SUMMARY

Machine learning systems generally depend on large sets of relevant labelled training data to train computerized systems to assist in assessing, diagnosing, or making predictions based on medical image data. However, for new and potentially promising treatments, large sets of labeled medical image data corresponding to patients who have undergone such treatments and have known outcomes are generally not available.

Embodiments of the present disclosure include a computerized pipeline system and method that may be used in situations where the medical image datasets of highest relevance are necessarily relatively small. For example, a cohort of interest might include participants (or candidates for participation) in a clinical trial for a new therapeutic treatment for a particular disease. The new treatment might include, for example, administering new drug, a new combination of drugs, and/or a using new protocol for treating the relevant disease. For example, a small dataset might include images from only 100-200 patients or even fewer than 100 patients.

The challenge posed by such small medical image datasets is that it is generally too difficult or not possible to effectively train a deep learning network from scratch to make sufficiently accurate predictions using such a small amount of training data. However, it may be possible to use such a small dataset to fine-tune/train a deep learning network that has a feature extraction portion (and/or other portions) that have been pre-trained on other datasets, preferably, a series of datasets starting with large, less relevant datasets and continuing with increasingly relevant (and often smaller) datasets.

For many diseases, such as particular cancers, there are large publicly available medical image datasets that might correspond to medical images (e.g., CT scans) from more than 20,000, more than 30,000 or even more than 70,000-100,000 individuals. Although such datasets will typically identify the type of disease (e.g., type of cancer), they will not necessarily also identify other specific information that might be needed for using fully supervised learning for predicting responses to various treatments. Thus, such datasets might be "unlabeled" and/or less relevant to a cohort of interest than other, smaller datasets in the sense that specific known information regarding treatment results or even identifying specific tumor genotypes within a specific type of cancer (e.g., lung), might not be available.

However, such large, unlabeled datasets can be effectively used as part of a pipeline system for developing a trained network using successively more relevant (and potentially significantly smaller) datasets for developing a trained deep learning network for analyzing data corresponding to a cohort of interest such as candidates or participants in a clinical trial for a particular new treatment.

In one embodiment of a pipeline system in accordance with the present disclosure, a first deep learning network is used to perform self-supervised learning (which does not require labeled training data) on a large medical image dataset to begin training a feature extraction portion (and/or other portions) of a deep learning network. In one example, a contrastive learning network is used. However, in other implementations consistent with the principles of this disclosure, a first deep learning network in the pipeline might be configured to implement other types of self-supervised learning. In other alternatives, it might be configured to implement a learning type other than self-supervised learning.

In selected embodiments, subsequent datasets of increasing relevance to a cohort of interest can be used to train, in succession, additional deep learning networks in the pipeline. These additional networks can be configured to use supervised learning, which, in some examples, includes attention-based multiple instance learning. Learned weights can be transferred from a feature extraction portion (and/or additional portions) of one network in the pipeline to a feature extraction portion (and/or additional portions) of a next network in the pipeline until a final, trained network is provided that can improve analysis of a relatively small dataset, for example, a dataset comprising a cohort of interest including candidates for, or participants in, a clinical trial of a new treatment.

In a broad sense, embodiments of the present disclosure illustrate a training pipeline comprising successive training of successive deep learning (or other machine learning) networks using successive data sets from less relevant to more relevant datasets with respect to a cohort of interest to improve predictions for whether and/or how a particular patient will respond to a new treatment. Other aspects of the disclosure are more fully discussed below.

While the embodiments are described with reference to the above drawings, the drawings are intended to be illustrative, and other embodiments are consistent with the spirit, and within the scope, of the disclosure.

DETAILED DESCRIPTION

The various embodiments now will be described more fully hereinafter with reference to the accompanying drawings, which form a part hereof, and which show, by way of illustration, specific examples of practicing the embodiments. This specification may, however, be embodied in many different forms and should not be construed as limited to the embodiments set forth herein; rather, these embodiments are provided so that this specification will be thorough and complete, and will fully convey the scope of the disclosure to those skilled in the art. Among other things, this specification may be embodied as methods or devices. Accordingly, any of the various embodiments herein may take the form of an entirely hardware embodiment, an entirely software embodiment or an embodiment combining software and hardware aspects. The following specification is, therefore, not to be taken in a limiting sense.

Figure 1:
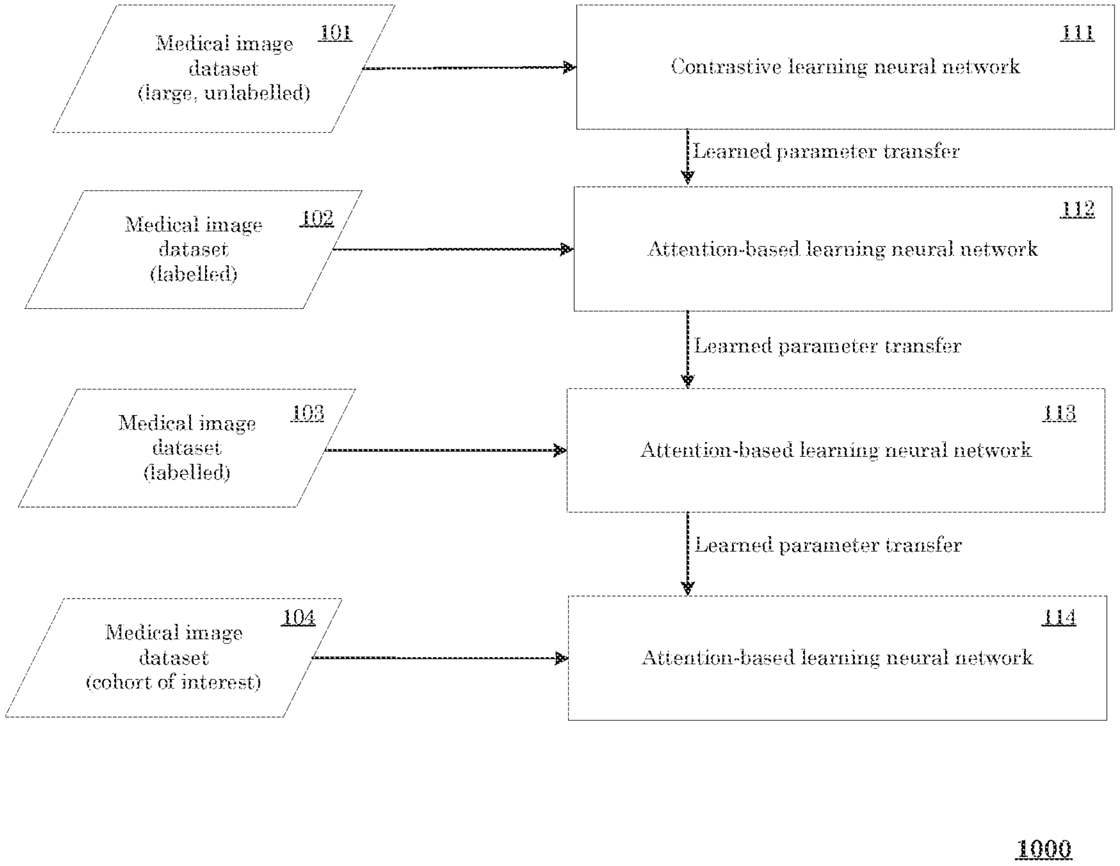
FIG. 1 illustrates a computerized pipeline system for developing a trained computerized deep learning network to make treatment response predictions using medical images corresponding to a cohort of interest including patients in, or candidates for being in, a clinical trial of a new treatment.

FIG. 1 illustrates a computerized pipeline system 1000 for developing a trained computerized deep learning network (or other computerized machine learning model) to make treatment response predictions (or other predictions) using medical images corresponding to a cohort of interest including patients in, or candidates for being in, a clinical trial of a new treatment (or of a new combination of treatments).

FIG. 1 is illustrated and described using the example of a series of neural networks 111, 112, 113, and 114. However, the underlining principles are applicable to other deep learning or machine learning computer systems, whether or not those systems include any neural network processing layers. A "neural network" in this example, simply means a computerized system that implements machine learning processing including one or more processing layers or elements known as neural network layer or elements. In various examples, this might include feed forward neural network layers (also known as fully-connected layers), convolutional neural network layers (which may or may not include residual connections), recurrent neural networks, or other types of neural network layers or elements. Such computerized machine learning systems are referred to herein as "neural networks" if the system includes any processing layer or element known to be a type of neural network processing layer or element. Even if such a system has many additional components or layers other than the neural network elements or layers, it will be referred to herein as a "neural network." Again, however, those skilled in the art will understand that certain inventive principles of the illustrated embodiment are applicable to other types of machine learning systems embodying the disclosure, even if those systems do not include any neural network components.

Specifically, pipeline system 1000 includes a series of respective neural networks (which could also be referred to as neural network modules, deep learning modules, and/or machine learning modules) 111, 112, 113, and 114. Respective medical image datasets 101, 102, 103, and 104 are used, in succession, to respectively train neural networks 111, 112, 113, and 114. In this example, the pipeline shows four neural networks in the pipeline system. However, in alternative implementations, more or fewer neural networks (or other types of machine learning modules), and more or fewer datasets could be used.

Pipeline system 1000 is tailored for use in situations where the medical image dataset of highest relevance, 104, is necessarily relatively small as it relates to a cohort of interest typically including participants (or candidates for participation) in a clinical trial for a new therapeutic treatment for a particular disease, for example, administering new drug, a new combination of drugs, and/or a using new protocol for treating the relevant disease. For example, a small dataset such as dataset 104 might include images from only 100-200 patients. In many examples, it might even correspond to images from less than 100 patients.

The challenge posed by such small medical image datasets is that it is generally too difficult or not possible to effectively train a deep learning network from scratch to make sufficiently accurate predictions using such a small amount of training data. However, it is possible to use such a small dataset to fine-tune/train a deep learning network that has a feature extraction portion that has been pre-trained (or has weights that have been transferred from an appropriately pre-trained network) on other datasets, preferably, a series of datasets starting with large, less relevant datasets and continuing with increasingly relevant (and typically smaller) datasets.

In the illustrated example, dataset 101 is a large, publicly available dataset. For many diseases, such as particular cancers, there are large publicly available medical image datasets that might correspond to medical images (e.g., CT scans) from more than 20,000, more than 30,000 or even more than 70,000-100,000 individuals. Although such datasets will typically identify the type of cancer, they will not necessarily also identify other specific information that might be needed for using fully supervised learning for predicting responses to various treatments. Thus, such datasets might be "unlabeled" in the sense that specific known information regarding treatment results or even identifying specific tumor genotypes within a specific type of cancer (e.g., lung), might not be available.

Although a dataset 101 might be labeled for some purposes, in the specific example described herein, it is not labeled for the specific purpose of training a treatment response classifier (or if it does have treatment response information, the corresponding treatment and/or cancer information is not relevant enough to the cohort of interest to use the labels for useful training purposes).

However, even if dataset 101 is not labeled (or otherwise does not have associated information that is sufficiently relevant enough for fully supervised learning), it can be effectively used for self-supervised learning to, for example, pre-train a feature extractor to extract relevant features from a computerized tomography (CT) scan (or other medical image) in the context of cancer or another other disease. Therefore, in pipeline system 1000, first deep learning network 111 performs self-supervised learning (which does not require the use of labeled training data) to begin training a feature extraction portion of deep learning network 111 using dataset 101. As further described in the context of FIG. 2 below, in this example, deep learning network 111 is configured to implement contrastive learning. However, in other implementations consistent with the principles of this disclosure, a first deep learning network in the pipeline might be configured to implement other types of self-supervised learning.

At least a portion of the learned parameters (sometimes referred to as weights, kernel values, filter values, or other names) that result from conducting self-supervised learning using contrast learning neural network 111 and medical image dataset 101 are transferred to second network 112. In this example, network 112 is an attention-based multi-instance deep learning network.

In pipeline system 1000, second network 112 is trained by medical image dataset 102. In this example, medical image dataset 102 is a labeled dataset and network 112 carries out attention-based supervised learning using medical image dataset 102 as described further in the context of FIG. 3.

In the illustrated example, dataset 102 is a smaller and more relevant dataset than dataset 101 with more corresponding relevant information. For example, it might be a commercial dataset (i.e., private) that includes treatment outcomes corresponding to the medical images. It might be in the context of the same disease or a similar disease as the disease corresponding to the cohort of interest, but the treatment and other aspects surrounding the data are different. After second network 112 is trained using medical image dataset 102, at least some of the resulting learned parameters are transferred to third deep learning network 113, which, in this example, is also an attention-based multi-instance deep learning network.

In pipeline system 1000, third network 113 is trained by medical image dataset 103. In this example, medical image dataset 103 is a labeled dataset corresponding to a clinical cohort that is not the cohort of interest, but that is more relevant to the cohort of interest than is dataset 102. In one example, medical image dataset 103 corresponds to a clinical trial cohort that has received a treatment that has some relevance to the treatment to be administered to the cohort of interest, but is not the same treatment. In this example, the clinical trial corresponding to dataset 103 has similar inclusion/exclusion criteria as the clinical trial for the new treatment to be administered to the cohort of interest.

After third network 113 is trained using medical image dataset 103, at least some of the resulting learned parameters are transferred to a final deep learning network 114, which, in this example, is also an attention-based multi-instance deep learning network.

Final deep learning network 114 is fine-tuned (further trained) using medical image dataset 104 which corresponds to at least a portion of the cohort of interest whose members are in, or are candidates for being in, a clinical trial of the new treatment. In one example, medical dataset 104 corresponds to a portion of the cohort of interest that has already received the new treatment and some data regarding response to that treatment is available.

After fine-tuning (i.e., training) of final network 114 using medical image dataset 104, network 114 can then be used to assist in predicting treatment responses for other members of the cohort of interest using medical images that correspond to those other members of the cohort of interest. In this manner, a final network such as network 114 that has been developed using pipeline system 1000 can allow for improved selection of participants in the relevant ongoing clinical trial or in future clinical trials involving the same or similar treatment.

The illustrated example of a pipeline system is described herein in terms of relevant learned weights being transferred from one deep learning network to a next deep learning network in the pipeline. However, one skilled in the art will understand that, in some instances (for example, when successive networks in the pipeline have the same architecture), this can be considered equivalent to successively training the same network first with one dataset and then with another dataset or, as another example, successively training the same network first on one data set and then re-initializing weights of some parts of the network (e.g., attention and classification layers, in which weights from training on a prior dataset are not retained when starting training on a the next data set in the pipeline) but not others (e.g., feature extraction layers, in which weights from training on a prior dataset are retained as starting values for training on the next dataset) when beginning training with next dataset. Such examples are considered consistent with the spirit and scope of the present disclosure.

Figure 2:
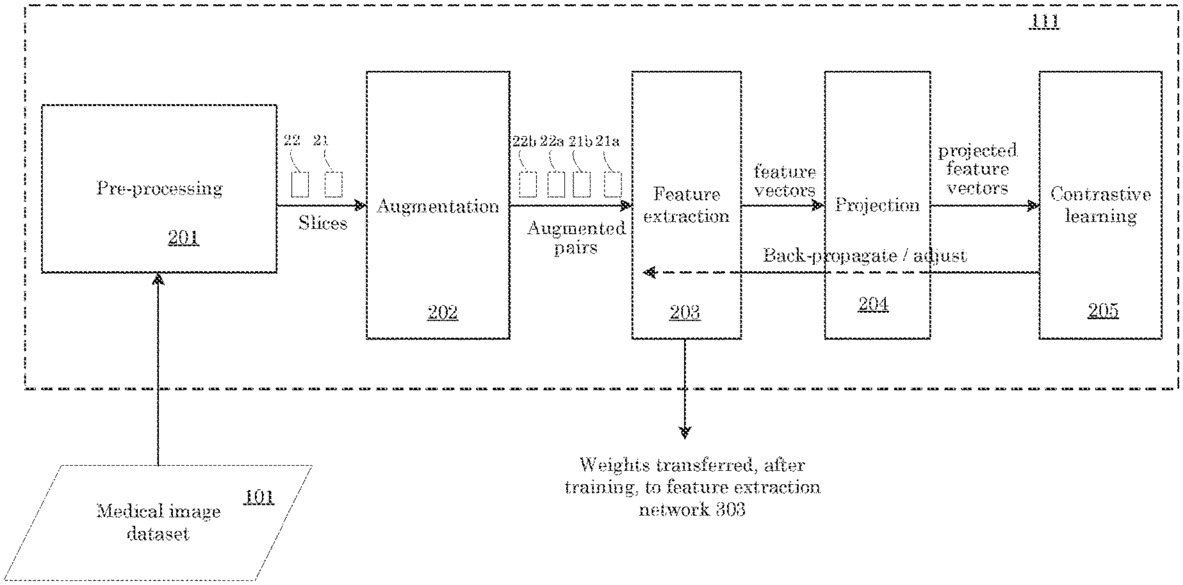
FIG. 2 is a block diagram illustrating the architecture of a self-supervised learning neural network of the embodiment of FIG. 1.

FIG. 2 is a block diagram illustrating the architecture of self-supervised learning neural network 111 (one example of a deep learning network consistent with a first deep learning network in a pipeline system embodying the underlying principles of the present disclosure) of the pipeline system 1000. Specifically, network 111 comprises pre-processing block 201, augmentation block 202, feature extraction network 203, projection network 204, and contrastive learning module 205.

Contrastive learning network 111 illustrated in FIG. 2 is similar to the contrastive learning network disclosed in applicant's co-pending U.S. Provisional Application No. 63/301,023 filed on Jan. 19, 2022 and hereby incorporated by reference in its entirety. Contrastive learning network 111 of the present disclosure is adapted to process data from medical images such as, for example, CT scans.

Pre-processing module 201 receives data from medical image dataset 101 and preprocesses it to provide slices such as slice 21 and slice 22, to augmentation module 202. Additional details of pre-processing module 201 will be discussed in the context of FIG. 4. Slices 22 and 21 are pre-processed pixel data corresponding to separate 2D slices, each 2D slice corresponding to a slice of the 3D CT data corresponding to an axial, coronal, or sagittal view.

Augmentation module 202 receives the pre-processed slices and may perform two different executions of an augmentation process on each slice to generate two different augmented versions of each slice. For example, in the illustrated example, augmentation module 202 receives two different slices 21 and 22 and, from slice 21, generates augmented slice 21*a* and augmented slice 21*b*, corresponding to two different iterations of an augmentation process, and, in similar fashion, from slice 22, generates augmented slice 22*a* and augmented slice 12*b*, also corresponding to two different iterations of the augmentation process. In one example, an augmentation process might include a series of steps performed on a slice such as: random cropping followed by resizing to the original size; random horizontal and/or vertical flipping; color jittering using randomly selected multipliers within a specified range for brightness, contrast, hue, and saturation; and/or randomly converting the image slice to grayscale (e.g., with a 0.5 probability). Such a process could be performed twice on the same slice (e.g., slice 21) to generate two different augmented versions of the slice (e.g., 21*a* and 21*b*).

In the illustrated example, two augmented slice pairs are generated from each slice fed into augmentation module 202. However, additional augmented slice versions can be generated from each slice.

Augmented slices are processed by feature extraction network 203. Feature extraction network 203 may based on the convolutional layers and the average pooling layer of ResNet 18, an 18-layer residual network as described in He et al., Deep Residual Learning for Image Recognition, available at arXiv:1512.03385v1, 10 Dec. 2015, incorporated herein by reference ("ResNet Paper"). The classification layers (fully connected layers and softmax layer) of ResNet 18 are not utilized, but are replaced by projection network 204. However, this is just an example. Different size and/or types of feature extraction networks can be used consistent with the principles of the present disclosure.

Feature extraction network 203 provides feature vectors (one per augmented slice) to projection network 204. Projection network (further described below in the context of FIG. 3) 204 processes the feature vectors and provides projected feature vectors to contrastive learning module 205.

Contrastive learning module 205 applies a loss function to compute a loss measure for features vectors corresponding to processed slices in a same batch. The loss measure can be related differences between feature vectors derived from different augmented versions of the same slice in the batch and is also related to differences between feature vectors corresponding to augmented versions of different slice in the batch. The loss is then back propagated through projection network 204 and feature extraction network 203 and used to adjust learnable parameters (weights) of those networks. To put it simply, as the system learns to produce better feature vectors, it decreases the difference between feature vectors from different augmented versions of the same slice while increasing the difference between feature vectors from augmented versions of different slices.

Contrastive learning module 205 may implement the "SimCLR" contrastive learning processing set forth in Chen et al., A Simple Framework for Contrastive Learning of Visual Representation, Proceedings of the 37th International Conference on Machine Learning, Vienna, PMLR 119, 2020, incorporated herein by reference ("SimCLR Paper"). Specifically, the NT-Xent loss referenced therein may be used as the loss function of contrastive learning module 205.

Figure 3:
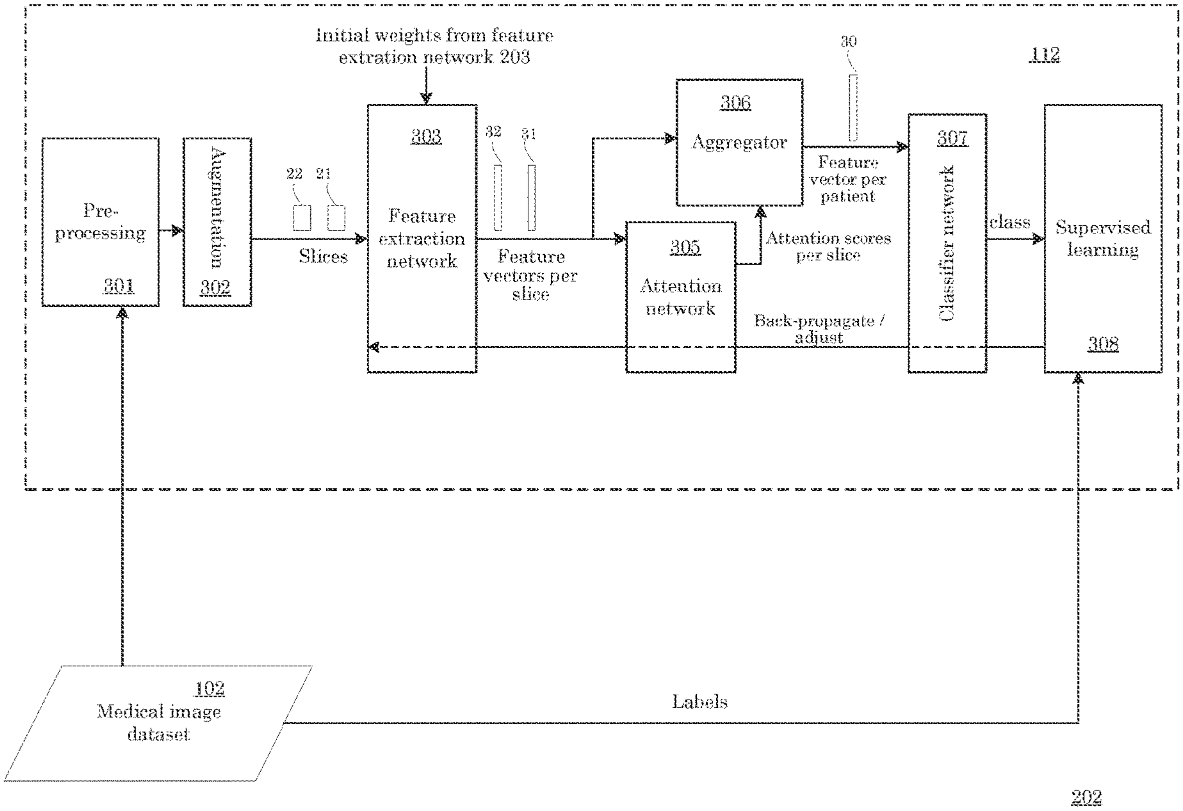
FIG. 3 is a block diagram illustrating the architecture of an attention-based learning network of the embodiment of FIG. 1.

FIG. 3 is a block diagram illustrating the architecture of attention-based learning network 112 (one example of a deep learning network consistent with a second deep learning network in a pipeline system embodying the underlying principles of the present disclosure) of the pipeline system 1000. Specifically, network 112 comprises pre-processing block 301, augmentation module 302, feature extraction network 303, attention network 305, aggregator 306, classifier network 307 and supervised learning module 308.

In the illustrated example, pre-processing block 301 is substantially similar to pre-processing block 301 of FIG. 2 and is further discussed below in the context of FIG. 4.

In one example, augmentation module 302 implements some but not all of the augmentation steps implemented by augmentation module 202 in FIG. 2. For example, augmentation module 302 might implement color jittering and horizontal and vertical flipping but not the other augmentation steps of augmentation module 202. In other examples, the same augmentations are used. In other examples, some augmentation steps implemented by augmentation module 302 are different than any of the steps of augmentation module 202. Those skilled in the art will recognized that, in the context of attention-based learning networks 112-114 (or other deep learning networks), augmentation is potentially useful for enhancing training robustness. However, alternatively, augmentation may or may not be used during supervised learning without necessarily departing from the spirit and scope of the present disclosure. In the illustrated embodiment, although augmentation is applied to training data used during training attention-based networks 112-114, when a final, fully trained network is applied to non-training medical image data for making predictions to assist decision-making, augmentation processing is not applied to the analyzed medical image data.

In the illustrated example, the details of feature extraction network 303 are substantially the same as those of feature extraction network 203 in FIG. 2 as described above. However, the architecture of those blocks could be different for different steps in a deep learning pipeline consistent with the present disclosure. For example, if a first data set used to train a first network in a pipeline is different (e.g., different type of images, different data dimensions, etc.) than a second data set used to train a next network in the pipeline, then the pre-processing and/or feature extraction portions of each network might be different.

In the example illustrated above, weights from feature extraction network 203 learned in training deep learning network 111 are transferred to feature extraction network 303 prior to training deep learning network 112 using data set 102. In the current example, feature extraction networks in each deep learning network 111, 112, 113, and 114 have the same architecture and dimensions. So weights learned in training each network in the pipeline can be transferred to provide all of the initial weights the feature extraction portion of the next deep learning network in the pipeline. However, even if feature extraction networks are different from one pipeline network to another, weights from a prior network in the pipeline can be transferred to comparable positions in a next network in the pipeline and, for example, any other positions in the next network can be initialized at zero or at some other value prior to training the next network. If needed, weights can be further processed during transfer via other techniques such as averaging, interpolation, or other methods so that the benefit of training feature extraction portions of a prior network can benefit training of the next network in the pipeline.

Continuing with the description of FIG. 3, feature extraction network 303 receives pre-processed slices such as slices 21 and 22 and processes them to extract feature vectors for each slice such as feature vectors 31 and 32. Feature vectors for each slice are fed to attention network 305 and to aggregation function 306. In this example, attention network 305 is simply a feed forward neural network comprising one or more fully connected layers with corresponding weights. The input layer size corresponds to the feature vector size and the output layer provides a single attention value for each slice. The output score (attention value) is normalized to be no less than 0 and no greater than 1.

Aggregator 306 multiplies each slice's feature vector by its corresponding attention score and then averages all feature vectors for a given CT scan of a patient to produce a summarized feature vector 30 such that one summarized feature vector is produced for each patient's CT scan. In the current example, summarized feature vector 30 will have the same dimensions as a feature vector for an individual slice. E.g., summarized feature vector 30 will have the same dimensions as single slice's feature vector such as feature vector 31. But in alternative examples, the sizes of summarized feature vectors do not necessarily exactly match the size of feature vectors for individual slices.

Summarized feature vectors (one for each patient's CT scan) are then provided to classifier network 307 (which, in this example, includes a typical feed forward network of one or more full connected layers) which produces a prediction value (or class) for each summarized feature vector. Supervised learning module 308 uses a loss function to compute a loss value based on a label corresponding to the relevant CT scan in dataset 102 and based on the class value provided by classifier network 307. Depending on the prediction type, different loss functions can be used. For example, if the prediction is in the form of survival time, or time to recurrence (which can be one of many values, e.g., a number of weeks), a cross-entropy loss function can be used. However, if the prediction is binary (e.g., response or no response), then a binary cross-entropy loss function can be used. These are just examples. Various loss functions for supervised learning are within the capability of one skilled in the art and a particular loss function used is not intended to limit the broader aspects of the present disclosure.

Supervised learning module 308 then back propagates the loss value (sometimes referred to as error value) through classifier network 307, attention network 305, and feature extraction network 303 and uses it to adjust weights (learnable parameters) in those networks. Various known techniques for backpropagation and weight adjustment can be used and learning rates, and other learning parameters can be selected and modified to enhance performance for a particular application.

In one example, the overall architecture of deep learning network 112, after pre-processing block 301, is based on aspects of the attention-based multi-instance deep learning architecture shown in Isle et al., *Attention-based Deep Multiple Instance Learning*, published at arXiv: 1802.04712v4 [cs.LG] 28 Jun. 2018 (referenced herein as "the attention-based MI learning paper") and incorporated herein by reference in its entirety (see, e.g., FIG. 6*c* of that paper's appendix). However, this is just one example. In other examples, different network architectures might be used for different networks in a pipeline system consistent with the present disclosure (e.g., other attention-based architectures or types of deep learning networks other than attention-based networks).

In the specific example of pipeline system 1000 of FIG. 1, the architecture of third network 113 and final network 114 are the same as that shown for second network 112 illustrated in FIG. 3 and will not be separately discussed herein. However, note that the architecture of pipeline networks from a second network to a last network need not be identical.

Furthermore, in the specific example of pipeline system 1000 of FIG. 1, only the weights from feature extraction networks such as feature extraction network 303 are transferred from one network in the pipeline to another. For example, as those skilled in the art will appreciate, during training of network 112 shown in FIG. 3, weights will be learned in attention network 305 and classifier network 307 as well as in feature extraction network 303. However, in the present example, only the weights in feature extraction network 303 will be transferred to a feature extraction network of the next network in the pipeline (e.g., network 113 of FIG. 1). Weights for attention and classifier networks in subsequent deep learning networks in the pipeline will be re-initialized and retrained from scratch. However, weights from the feature extraction network will be transferred. Nevertheless, in alternative examples, feature extraction network weights and other weights (such as, for example, weights from classification network such as classifier 307) could be transferred to a next network in the pipeline prior to training the next network without necessarily departing from the principles of the present disclosure.

Figure 4:
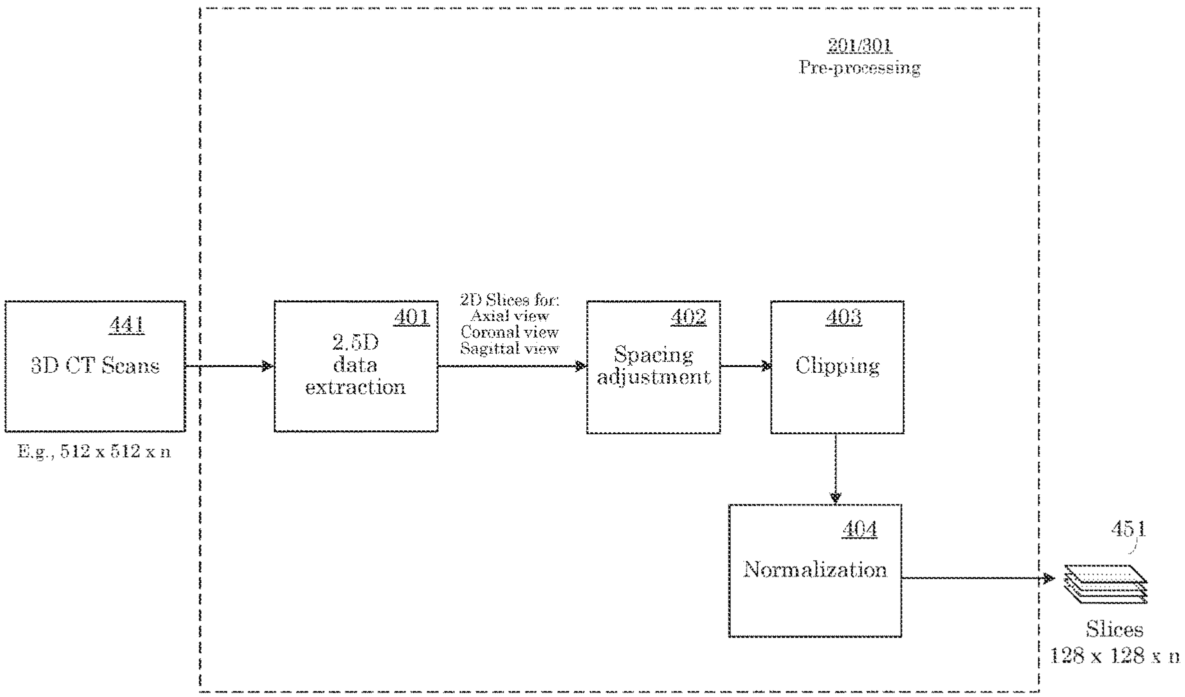
FIG. 4 illustrates further details of pre-processing carried out in the context of the medical image datasets of one example.

FIG. 4 illustrates further details of pre-processing block 201 of FIG. 2 (which are the same as details of pre-processing block 301 of FIG. 3). As shown, 3D CT scan data 441 (which can be, for example, part of a current dataset such as dataset 102) is provided to 2.5 data extraction module 401. In this example, module 401 takes the 3D data for a particular CT scan and extracts 2D slices from it including slices along the axial view, slices along the coronal view, and slices along the sagittal view. Those slices are then pre-processed by spacing adjustment module 402, clipping module 403, and normalization module 402.

Spacing adjustment module 402 performs processing to reduce the effects of different CT scanners having different x, y, and z spatial resolutions. Spacing adjustment techniques can be used as described in, for example, M. Anthimopoulos, S. Christodoulidis, L. Ebner, A. Christe and S. Mougiakakou, "Lung Pattern Classification for Interstitial Lung Diseases Using a Deep Convolutional Neural Network," in IEEE Transactions on Medical Imaging, vol. 35, no. 5, pp. 1207-1216, May 2016, doi: 10.1109/TMI.2016.2535865, incorporated herein by reference in its entirety. Clipping module 403 sets upper and lower limits on the Hounsfield Unit (HU) intensity value. In one example, for CT scans with HU intensity values ranging from −3000 to +3000, a lower limit of −1000 and an upper limit of 400 is applied. As one skilled in the art would appreciate, the selected values can vary in specific implementations without necessarily departing from the spirit and scope of the present disclosure. Normalization block 404 normalizes the HU values for each slice. In one example, HU values can be normalized between 0-1. In other examples, different scales can be used without departing from the spirit and scope of the present disclosure.

In the illustrated example, the size of 3D scan data 441 is 512×512×n where n is the number of cross sections in the CT scan data. The size of output slices 451 is 128×128×n where n is the number slices (including axial view slices, coronal view slices, and sagittal view slices) and each slice is 128×128 in size. However, these dimensions are just one example and others can be used.

Furthermore, as illustrated, each axial, coronal, or sagittal slice is not further sub-divided. For example, an entire slice across the portion of an axial (or coronal or sagittal) plane included in the image data is processed at the same time by processing phases of the relevant deep learning network in the pipeline. However, alternately, such slices could be further sub-divided into tiles and the individual tiles could be processed as units, without necessarily departing from the underlying principles of the present disclosure.

Figure 5:
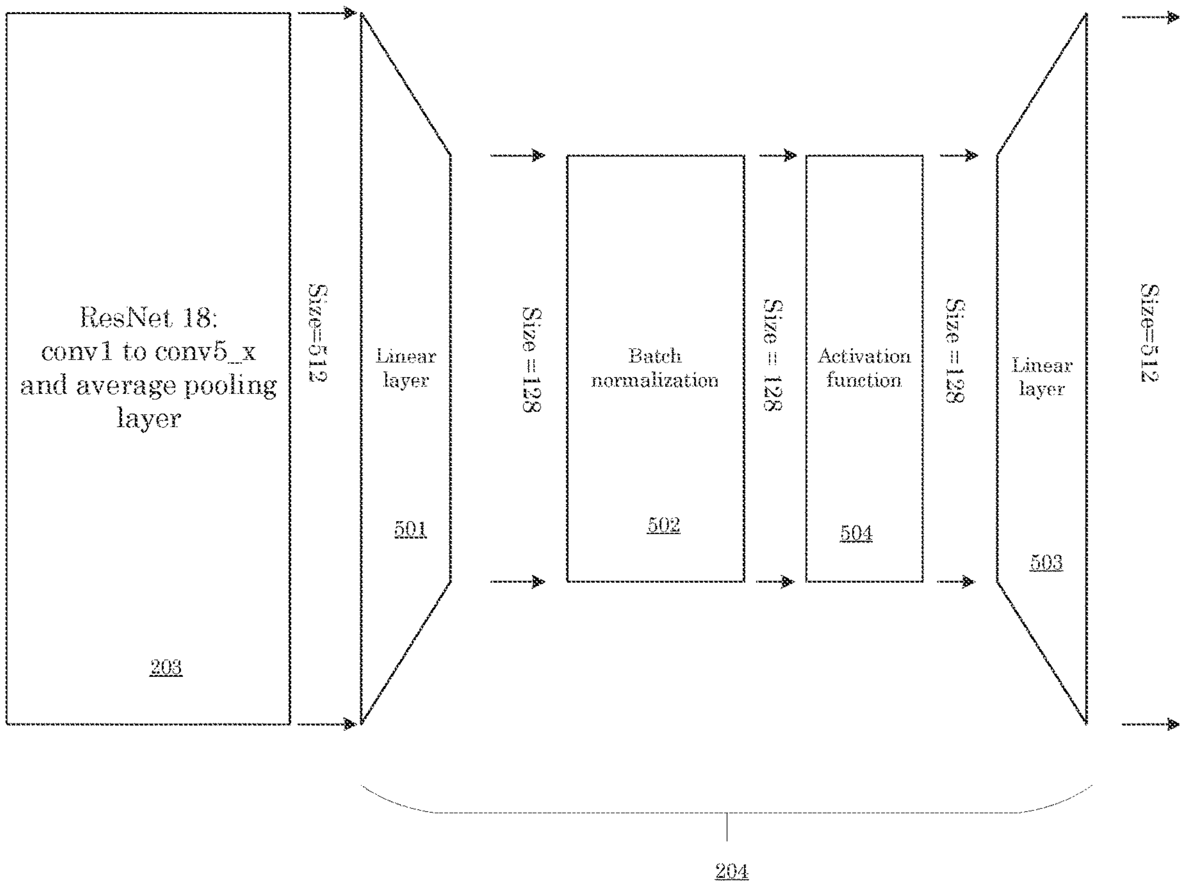
FIG. 5 illustrates further details of a feature extraction network and a projection network of the self-supervised learning network illustrated in FIG. 2.

FIG. 5 illustrates further details of feature extraction network 203 and projection network 204. Specifically, in the illustrated example, feature extraction network 203 uses the convolutional layers associated with con1, conv2_x, conv3_x, conv4_x, conv5_x, and the average pooling layer, but NOT the fully connected layers of the resnet 18 in the ResNet Paper. It also uses all skip connections associated with those layers in the ResNet Paper. In this example, feature extraction network 203 outputs feature vectors having 512 values to projection network 204.

Projection network 204 may comprise linear layer 501, batch normalization layer 502, activation layer 504, and linear layer 503. Linear layer 501 comprises an input layer and a fully connected hidden layer of 128 neurons (without activation functions). Thus linear layer 501 outputs a feature vector of size 128 to batch normalization layer 502. Batch normalization layer 502 performs standard batch normalization processing. After passing through batch normalization layer 502, the feature vector passes through activation function layer 504 implementing a non-linear activation function such as ReLu and then to linear layer 503 which comprises an input layer of size 128 and a fully connected hidden layer of 512 neurons (without activation functions), and which therefore projects the feature vector back up to 512 in size.

It will be understood that, in this context, "projection network" simply refers to the fact that the feature representations undergo changes in the number of dimensions used for representation as they are passed through the network. In this example, the projected features have the same dimensions as the input features but have been obtained through a process in which the feature representations were first projected into a lower dimensional representation and then, after batch normalization, projected back up into a representation having the same number of dimensions as the input representations. Alternatively, use of a projection network may be omitted such as that illustrated and described herein, better results are obtained by using a projection network and batch normalization before passing resulting feature vectors to a contrastive learning module.

Figure 6:
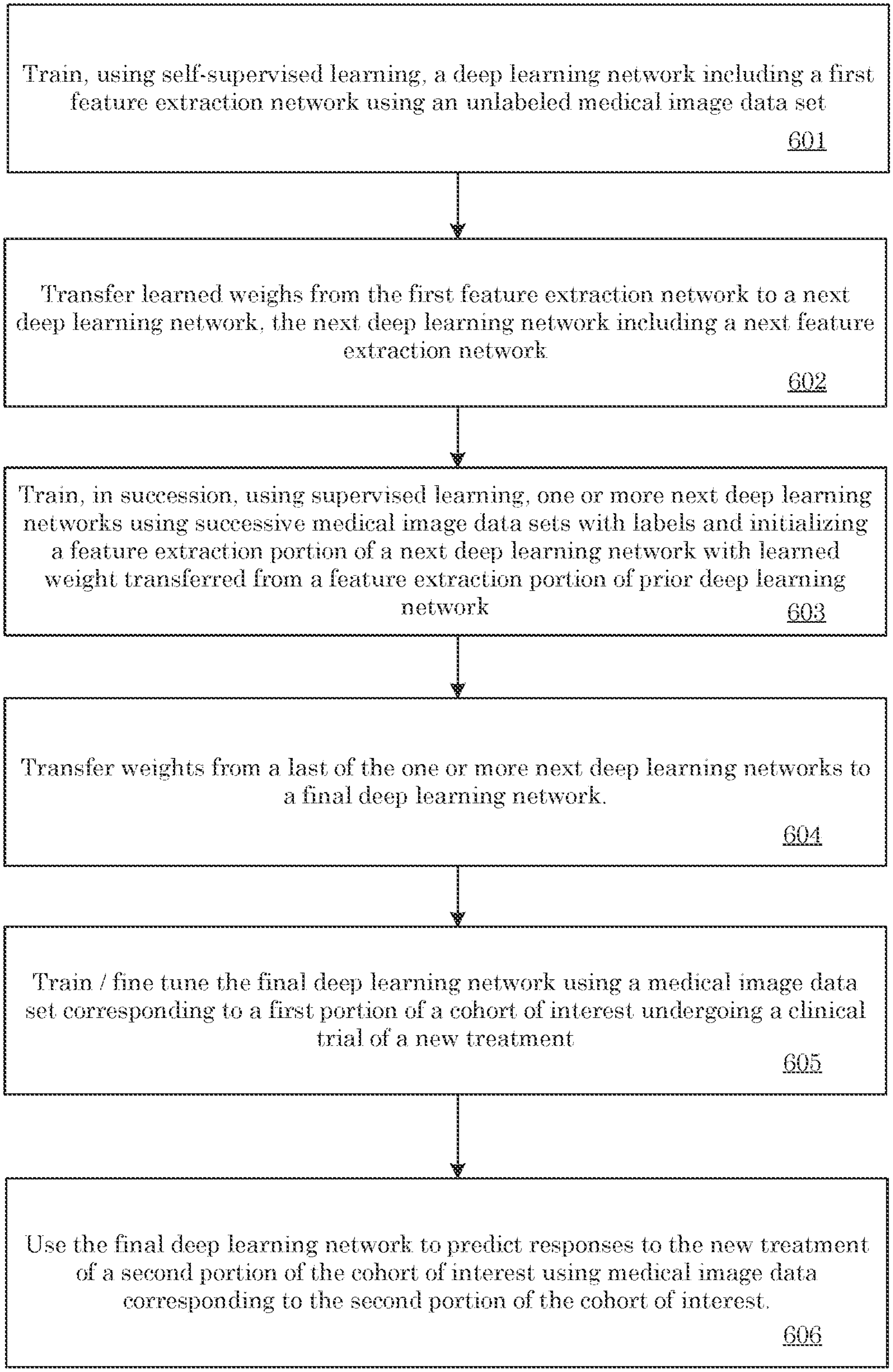
FIG. 6 illustrates a computer-implemented method for providing final, trained deep learning network to predict responses in members of a cohort of interest to a new treatment using a pipeline system such as the system of FIG. 1.

FIG. 6 illustrates a computer-implemented method 6000 for providing final, trained deep learning network to predict responses in members of a cohort of interest to a new treatment using a pipeline system such as system 1000 of FIG. 1.

Step 601 includes training a first deep learning network using a first medical image dataset. In this particular example, contrastive self-supervised learning is used to train a first feature extractor without requiring use of labels from the training dataset (the first medical image dataset).

Step 602 includes transferring weights of the first feature extractor that are learned from self-supervised training of the first deep learning network to a feature extractor of a next deep learning network in a pipeline training system.

Step 603 includes training, in succession, one or more additional next deep learning networks using successive next medical image data sets and transferring weights from a feature extractor of one network of one network in the pipeline to a feature extractor of a next network in the pipeline. Again, in the illustrated example, only weights of the feature extraction portion of each deep learning network are transferred from one network to the next in the pipeline. However, in alternative examples, weight of other portions of the network (e.g., classification portions) could be transferred as well. As previously discussed, successive data sets in the pipeline are increasingly relevant to the cohort of interest for which the final network in the pipeline is to be trained.

Step 604 includes transferring weights to a final network in the pipeline. Step 605 includes fine tuning the final network using a data from a first portion of the cohort of interest in a clinical trial for the relevant new treatment.

Step 606 includes using the final trained deep learning network to make response predictions based on medical images corresponding to members of a second portion of the cohort of interest.

Results and Implications

An example of a final, trained network provided by examples of the pipeline system and method disclosed herein have been tested on data from a cohort of interest in the context of a clinical trial for lung cancer treatment. The available testing data on a cohort of interest of less than 100 patients showed improvement in candidate selection for treatment relative to existing methods. Specifically, in one example of the tested data, use of the radiomic artificial intelligence methods described herein selected clinical trial candidates for treatment that exhibited a higher new treatment response rate, 53%, than did clinical trial candidates selected by existing methods, which showed a 36% response rate. In short, the illustrated systems and methods have initially demonstrated a significant improvement in candidate selection for clinical trials. This technology can therefore help clinical trials better identify which treatment work best with which individuals and therefore can potentially help accelerate development and implementation of effective new treatments for serious diseases.

Figure 7:
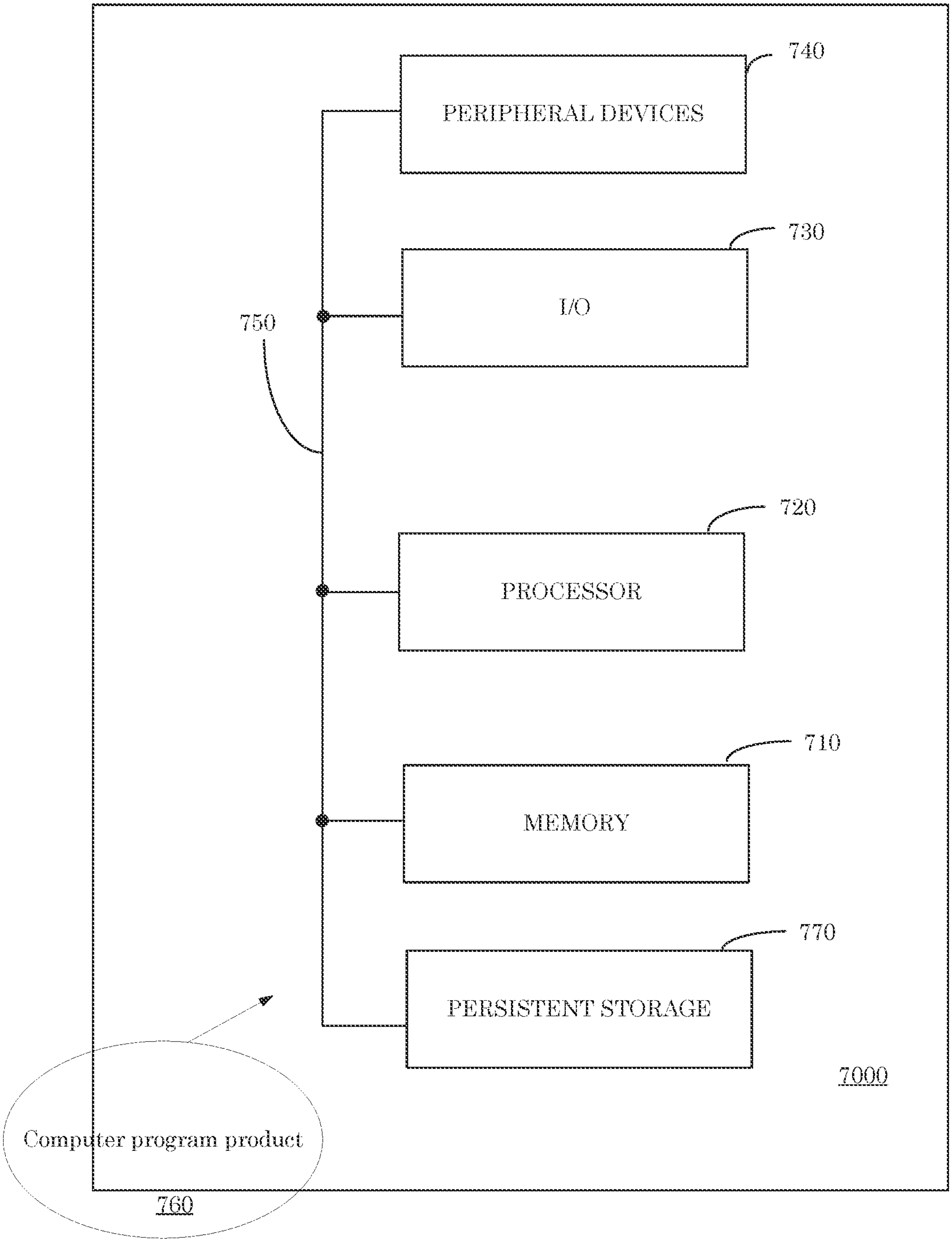
FIG. 7 shows an example of a computer system 7000, one or more of which may be used to implement one or more of the apparatuses, systems, and methods illustrated herein.

FIG. 7 shows an example of a computer system 7000, one or more of which may be used to implement one or more of the apparatuses, systems, and methods illustrated herein. Computer system 7000 executes instruction code contained in a computer program product 760. Computer program product 760 comprises executable code in an electronically readable medium that may instruct one or more computers such as computer system 7000 to perform processing that accomplishes the exemplary method steps performed.

The electronically readable medium may be any transitory or non-transitory medium that stores information electronically and may be accessed locally or remotely, for example via a network connection. The medium may include a plurality of geographically dispersed media each configured to store different parts of the executable code at different locations and/or at different times. The executable instruction code in an electronically readable medium directs the illustrated computer system 7000 to carry out various exemplary tasks described herein. The executable code for directing the carrying out of tasks described herein would be typically realized in software. However, it will be appreciated by those skilled in the art, that computers or other electronic devices might utilize code realized in hardware to perform many or all the identified tasks. Those skilled in the art will understand that many variations on executable code may be found that implement exemplary methods within the spirit and the scope of the disclosure.

The code or a copy of the code contained in computer program product 760 may reside in one or more storage persistent media (not separately shown) communicatively coupled to system 7000 for loading and storage in persistent storage device 770 and/or memory 710 for execution by processor 720. Computer system 700 also includes I/O subsystem 730 and peripheral devices 740. I/O subsystem 730, peripheral devices 740, processor 720, memory 710, and persistent storage device 770 are coupled via bus 750. Like persistent storage device 770 and any other persistent storage that might contain computer program product 760, memory 710 is a non-transitory media (even if implemented as a typical volatile computer memory device). Moreover, those skilled in the art will appreciate that in addition to storing computer program product 760 for carrying out processing described herein, memory 710 and/or persistent storage device 770 may be configured to store the various data elements referenced and illustrated herein.

Those skilled in the art will appreciate computer system 7000 illustrates just one example of a system in which a computer program product in accordance with the disclosure may be implemented. To cite but one example, execution of instructions contained in a computer program product may be distributed over multiple computers, such as, for example, over the computers of a distributed computing network.

Instructions for implementing an artificial neural network or other deep learning network may reside in computer program product 760. When processor 720 is executing the instructions of computer program product 760, the instructions, or a portion thereof, are typically loaded into working memory 710 from which the instructions are readily accessed by processor 720.

Processor 720 may comprise multiple processors which may comprise respective additional working memories (additional processors and memories not individually illustrated) including one or more graphics processing units (GPUs) comprising at least thousands of arithmetic logic units supporting parallel computations on a large scale. GPUs are often utilized in deep learning applications because they can perform the relevant processing tasks more efficiently than can typical general-purpose processors (CPUs). Processor 720 may additionally or alternatively comprise one or more specialized processing units comprising systolic arrays and/or other hardware arrangements that support efficient parallel processing. Such specialized hardware may work in conjunction with a CPU and/or GPU to carry out the various processing described herein. Such specialized hardware may comprise application specific integrated circuits and the like (which may refer to a portion of an integrated circuit that is application-specific), field programmable gate arrays and the like, or combinations thereof. However, a processor such as processor 720 may be implemented as one or more general purpose processors (preferably having multiple cores) without necessarily departing from the spirit and scope of the present disclosure.

While the present disclosure has been particularly described with respect to the illustrated embodiments, it will be appreciated that various alterations, modifications, and adaptations may be made based on the disclosure and are intended to be within the scope of the disclosure. While the disclosure has been described in connection with what are presently considered to be the most practical and preferred embodiments, it is to be understood that the present disclosure is not limited to the disclosed embodiments but, on the contrary, is intended to cover various modifications and equivalent arrangements included within the scope of the underlying principles of the invention as described by the various embodiments reference above and below.

Additional Examples

In some instances, a method of, via a deep learning pipeline, generating a deep learning network configured to execute on one or more computers to use medical image data to generate predictions of therapeutic responses to a new treatment in members of a cohort of interest, the cohort of interest comprising candidates for receiving the new treatment in a clinical trial, comprises: training, in succession, a plurality of respective deep learning networks from a first deep learning network to a last deep learning network using respective medical image datasets having respective degrees of relevance to the cohort of interest; and transferring, in succession, learned parameters of one deep learning network of the plurality of respective deep learning networks to another deep learning network of the plurality of respective deep learning networks after training the one deep learning network with a one of the respective medical image datasets and before training the another deep learning network with another medical image dataset of the respective medical image datasets.

In some instances, the respective degrees of relevance to the cohort of interest increase from a first respective medical image dataset to a last respective medical image dataset used in training the respective deep learning networks. In some instances, the first medical image dataset is significantly larger than the last medical image dataset.

In some instances, a first medical image dataset of the respective medical image datasets comprises unlabeled medical image data. In some instances, the first deep learning network comprises a feature extraction network and a contrastive learning module. In some instances, the first deep learning network further comprises a projection network configured to receive feature vectors from the feature extraction network and to provide feature vectors to the contrastive learning module.

In some instances, each deep learning network of the plurality of respective deep learning networks from a second deep learning network to the last deep learning network comprises a feature extraction network and a classification network, and further wherein the second deep learning network to the last deep learning network is trained using supervised learning. In some instances, the each deep learning network from the second deep learning network to the last deep learning network further comprises an attention network. In some instances, the method further comprises, for each of the second deep learning network to the last deep learning network, combining output of the feature extraction layers and output of the attention network to provide a combined output to a classification network.

In some instances, the attention network comprises one or more fully-connected layers configured to generate an attention value for each feature vector.

In some instances, combining output of the feature extraction layers and output of the attention network comprises, for each feature vector obtained from data corresponding to a particular medical image, multiplying the each feature vector by a corresponding attention value; and the method comprises generating a summarized feature vector summarizing the results of combining outputs corresponding to the particular medical image. In some instances, the summarized feature vector is generated by averaging the results of multiplying each feature vector by the corresponding attention value. In some instances, the summarized feature vector is submitted to a classification network. In some instances, output of the classification network and labels corresponding to a current medical image dataset are used to compute an error based on a loss function and the error is used to adjust weights in a deep learning network currently being trained.

In some instances, the respective medical image datasets comprise computerized tomography (CT) scan data.

In some instances, the method further comprises pre-processing the respective medical image datasets to obtain pre-processed two-dimensional slices of the CT scan data wherein the pre-processed two dimensional slices include slices corresponding to one or more of axial views, coronal views, and sagittal views. In some instances, a pre-processed two-dimensional slice of the pre-processed two dimensional slices corresponds to one of a full axial view, a full coronal view, or a full sagittal view; and the pre-processed two-dimensional slices collectively include at least some axial views, at least some sagittal views, and at least some coronal views. In some instances, a pre-processed two-dimensional slice of the pre-processed two dimensional slices corresponds to a tile portion of a full axial view, a full coronal view, or a full sagittal view; and for each full axial view, full coronal view, and full sagittal view the pre-processed two-dimensional slices collectively include a plurality of tile portions. In some instances, pre-processing comprises one or more of space adjustment, clipping, and normalizing. In some instances, pre-processing comprises clipping and wherein clipping comprises setting upper and lower limits of a Hounsfield Unit (HU) intensity value. In some instances, for CT scans having HU intensity values ranging from −3000 to +3000, clipping comprises applying a lower HU intensity value limit of −1000 and an upper HU intensity value limit of 400.

In some instances, the new treatment comprises a treatment for lung cancer.

In some instances, the method further comprises: using the generated deep learning network to process medical images corresponding to the candidates for receiving the new treatment in the clinical trial to generate predictions of therapeutic responses to the new treatment.

In some instances, a computer program product stored in a non-transitory computer readable medium comprising instructions is configured to execute a method according to any of the foregoing instances using one or more computer processors.

In some instances, a computerized pipeline system comprising a series of successive computerized deep learning networks is configured to execute processing to execute a method according to any of the foregoing instances.

In some instances, a computer system comprises one or more computers coupled to a non-transitory computer readable medium storing instructions that are executable by one or more processors of the one or more computers to implement a deep learning network configured to use medical image data to generate predictions of therapeutic responses to a new treatment in members of a cohort of interest, the cohort of interest comprising candidates for receiving the new treatment in a clinical trial, the deep learning network having been trained using the method of any of the foregoing instances.

In some instances, a computer system comprises: a deep learning pipeline comprising one or more computers coupled to a non-transitory computer readable medium storing instructions that are executable by one or more processors of the one or more computers for training, in succession, a plurality of respective deep learning networks using respective medical image datasets, each respective medical image dataset having a respective degree of relevance to a cohort of interest, wherein training comprises: training a first deep learning network of the plurality of respective deep learning networks with one medical image dataset of the respective medical image datasets; transferring a plurality of learned parameters of the first deep learning network to a second deep learning network of the plurality of respective deep learning networks; and training the second deep learning network with another medical image dataset of the respective medical image datasets.

In some instances, training further comprises, from a next deep learning network of the plurality of deep learning networks to a last deep learning network of the plurality of respective deep learning networks: training, in succession, respective ones of the plurality of respective deep learning networks using respective medical image datasets having respective degrees of relevance to the cohort of interest; transferring, in succession, learned parameters of one deep learning network of the plurality of respective deep learning networks to another deep learning network of the plurality of respective deep learning networks after training the one deep learning network with a one of the respective medical image datasets and before training the another deep learning network with another medical image dataset of the respective medical image datasets.

In some instances, a first medical image dataset of the respective medical image datasets comprises unlabeled medical image data. In some instances, the first deep learning network comprises a feature extraction network and a contrastive learning module.

In some instances, each deep learning network of the plurality of respective deep learning networks from the second deep learning network to the last deep learning network comprises a feature extraction network and a classification network, and further wherein the second deep learning network to the last deep learning network is trained using supervised learning.

In some instances, the each deep learning network from the second deep learning network to the last deep learning network further comprises an attention network.

In some instances, the respective medical image datasets comprise computerized tomography (CT) scan data.

In some instances, training further comprises pre-processing the respective medical image datasets to obtain pre-processed two-dimensional slices of the CT scan data wherein the pre-processed two dimensional slices include slices corresponding to one or more of axial views, coronal views, and sagittal views.

In some instances, a pre-processed two-dimensional slice of the pre-processed two dimensional slices corresponds to one of a full axial view, a full coronal view, or a full sagittal view; and the pre-processed two-dimensional slices collectively include at least some axial views, at least some sagittal views, and at least some coronal views.

In some instances, a pre-processed two-dimensional slice of the pre-processed two dimensional slices corresponds to a tile portion of a full axial view, a full coronal view, or a full sagittal view; and for each full axial view, full coronal view, and full sagittal view, the pre-processed two-dimensional slices collectively include a plurality of tile portions.

In some instances, pre-processing comprises one or more of space adjustment, clipping, and normalizing. In some instances, pre-processing comprises clipping and wherein clipping comprises setting upper and lower limits of a Hounsfield Unit (HU) intensity value.

In some instances, for CT scans having HU intensity values ranging from −3000 to +3000, clipping comprises applying a lower HU intensity value limit of −1000 and an upper HU intensity value limit of 400.

In some instances, the new treatment comprises a treatment for lung cancer.

The invention claimed is:

1. A method of, via a deep learning pipeline, generating a deep learning network configured to execute on one or more computers to use medical image data to generate predictions of therapeutic responses to a new treatment in members of a cohort of interest, the cohort of interest comprising candidates for receiving the new treatment in a clinical trial, the method comprising:

training, in succession, a plurality of respective deep learning networks from a first deep learning network to a last deep learning network using respective medical image datasets having respective degrees of relevance to the cohort of interest; and transferring, in succession, learned parameters of one deep learning network of the plurality of respective deep learning networks to another deep learning network of the plurality of respective deep learning networks after training the one deep learning network with a one of the respective medical image datasets and before training the another deep learning network with another medical image dataset of the respective medical image datasets, wherein each deep learning network of the plurality of respective deep learning networks from a second deep learning network to the last deep learning network is trained using supervised learning and comprises: (a) a feature extraction network having feature extraction layers that generate one or more feature vectors, (b) a classification network, and (c) an attention network, and for each of the second deep learning network to the last deep learning network, combining output of the feature extraction layers and output of the attention network to provide a combined output to the classification network, by multiplying each feature vector by a corresponding attention value for each feature vector obtained from data corresponding to a particular medical image; and generating a summarized feature vector summarizing the results of combining outputs corresponding to the particular medical image.

2. The method of claim 1 wherein the respective degrees of relevance to the cohort of interest increase from a first respective medical image dataset to a last respective medical image dataset used in training the respective deep learning networks.

3. The method of claim 2 wherein the first medical image dataset is significantly larger than the last medical image dataset.

4. The method of claim 1 wherein a first medical image dataset of the respective medical image datasets comprises unlabeled medical image data.

5. The method of claim 4 wherein the first deep learning network comprises a feature extraction network and a contrastive learning module.

6. The method of claim 5 wherein the first deep learning network further comprises a projection network configured to receive feature vectors from the feature extraction network and to provide feature vectors to the contrastive learning module.

7. The method of claim 1 wherein the attention network comprises one or more fully-connected layers configured to generate an attention value for each feature vector.

8. The method of claim 1 wherein the summarized feature vector is generated by averaging the results of multiplying each feature vector by the corresponding attention value.

9. The method of claim 1 wherein the summarized feature vector is submitted to a classification network.

10. The method of claim 9 wherein output of the classification network and labels corresponding to a current medical image dataset are used to compute an error based on a loss function and the error is used to adjust weights in a deep learning network currently being trained.

11. The method of claim 1 wherein the respective medical image datasets comprise computerized tomography (CT) scan data.

12. The method of claim 11 further comprising pre-processing the respective medical image datasets to obtain pre-processed two-dimensional slices of the CT scan data wherein the pre-processed two-dimensional slices include slices corresponding to one or more of axial views, coronal views, and sagittal views, wherein:

a pre-processed two-dimensional slice of the pre-processed two dimensional slices corresponds to one of a full axial view, a full coronal view, or a full sagittal view; and the pre-processed two-dimensional slices collectively include at least some axial views, at least some sagittal views, and at least some coronal views.

13. The method of claim 11 further comprising pre-processing the respective medical image datasets to obtain pre-processed two-dimensional slices of the CT scan data wherein the pre-processed two dimensional slices include slices corresponding to one or more of axial views, coronal views, and sagittal views wherein:

a pre-processed two-dimensional slice of the pre-processed two dimensional slices corresponds to a tile portion of a full axial view, a full coronal view, or a full sagittal view; and for each full axial view, full coronal view, and full sagittal view the pre-processed two-dimensional slices collectively include a plurality of tile portions.

14. The method of claim 11 further comprising pre-processing the respective medical image datasets to obtain pre-processed two-dimensional slices of the CT scan data wherein the pre-processed two dimensional slices include slices corresponding to one or more of axial views, coronal views, and sagittal views, wherein pre-processing comprises one or more of space adjustment, clipping, and normalizing.

15. The method of claim 11 further comprising pre-processing the respective medical image datasets to obtain pre-processed two-dimensional slices of the CT scan data wherein the pre-processed two dimensional slices include slices corresponding to one or more of axial views, coronal views, and sagittal views, wherein pre-processing comprises clipping and wherein clipping comprises setting upper and lower limits of a Hounsfield Unit (HU) intensity value.

16. The method of claim 15 wherein, for CT scans having HU intensity values ranging from −3000 to +3000, clipping comprises applying a lower HU intensity value limit of −1000 and an upper HU intensity value limit of 400.

17. A computer system comprising:

a deep learning pipeline comprising one or more computers coupled to a non-transitory computer readable medium storing instructions that are executable by one or more processors of the one or more computers for training, in succession, a plurality of respective deep learning networks using respective radiology image datasets, each respective radiology image dataset having a respective degree of relevance to a cohort of interest, wherein training comprises:

training a first deep learning network of the plurality of respective deep learning networks with one radiology image dataset of the respective radiology image datasets;

transferring a plurality of learned parameters of the first deep learning network to a second deep learning network of the plurality of respective deep learning networks; and training the second deep learning network with another radiology image dataset of the respective radiology image datasets, wherein each deep learning network of the plurality of respective deep learning networks from the second deep learning network to a last deep learning network is trained using supervised learning and comprises: (a) a feature extraction network having feature extraction layers that generate one or more feature vectors, (b) a classification network, and (c) an attention network, and for each of the second deep learning network to the last deep learning network, combining output of the feature extraction layers and output of the attention network to provide a combined output to the classification network, by multiplying each feature vector by the corresponding attention value for each feature vector obtained from data corresponding to a particular radiology image; and generating a summarized feature vector summarizing the results of combining outputs corresponding to the particular radiology image.

18. The computer system of claim 17 wherein training further comprises, from the second deep learning network of the plurality of deep learning networks to the last deep learning network of the plurality of respective deep learning networks:

training, in succession, respective ones of the plurality of respective deep learning networks using respective radiology image datasets having respective degrees of relevance to the cohort of interest;

transferring, in succession, learned parameters of one deep learning network of the plurality of respective deep learning networks to another deep learning network of the plurality of respective deep learning networks after training the one deep learning network with a one of the respective radiology image datasets and before training the another deep learning network with another radiology image dataset of the respective radiology image datasets.

* * * * *